United States Patent [19]

Polis

[11] Patent Number: 5,672,725
[45] Date of Patent: Sep. 30, 1997

[54] PROCESS FOR PREPARING QUINONES

[75] Inventor: David W. Polis, Redondo Beach, Calif.

[73] Assignee: Hoechst Celanese Corp., Somerville, N.J.

[21] Appl. No.: 531,507

[22] Filed: Sep. 21, 1995

[51] Int. Cl.$^6$ ............................ C07C 50/04; C07C 50/02
[52] U.S. Cl. ............................................. 552/293; 552/291
[58] Field of Search ............................ 552/293, 291; 568/322, 811

[56] References Cited

U.S. PATENT DOCUMENTS 4,636,456  1/1987  Takahashi .
5,220,042  6/1993  Iwaki .
5,442,117  8/1995  Stahly .

*Primary Examiner*—José G. Dees
*Assistant Examiner*—Karl J. Puttlitz, Jr.
*Attorney, Agent, or Firm*—Palaiyur S. Kalyanaraman

[57] ABSTRACT

The invention provides a novel process to oxidize 1,4-dihydroxy aromatic compounds into the corresponding quinones using sulfuryl chloride as the oxidant. The process is simple and cost effective and provides an efficient way to synthesize hindered quinones.

15 Claims, No Drawings

PROCESS FOR PREPARING QUINONES

FIELD OF THE INVENTION

This application discloses a novel process for preparing, in high yields, cyclic enones generally, and quinones particularly. The process employs a reagent such as, for example, sulfuryl chloride to oxidize a suitable dihydroxy compound such as, for example, a hydroquinone. The inventive process advantageously offers simplicity of operation, plus low cost, while at the same time eliminating use of external solvents.

BACKGROUND OF THE INVENTION

The class of cyclic enones is well known in organic chemistry. Best known examples of cyclic enones are quinones such as, for example, the benzoquinones, naphthoquinones, anthraquinones, phenanthraquinones, and the like. 1,4-Benzoquinone is commonly referred to as quinone. Quinones are generally brightly colored compounds and have versatile applications in chemical synthesis, biological uses, as redox materials, as well as in industry. There are several review articles on the chemistry and applications of quinones including, for example, *Kirk-Othmer Encyclopedia of Chemical Technology*, Third ed., Vol. 19, pages 572–605, John Wiley & Sons, New York, 1982.

The synthesis of quinones is well documented. See, for example, J. Cason, *Synthesis of Benzoquinones by Oxidation*, in *Organic Synthesis*, Vol. IV, page 305, John Wiley & Sons, New York (1948). Quinones generally are prepared by oxidizing the appropriately disubstituted aromatic hydrocarbon derivatives, the substituents being hydroxyl or amino groups in the ortho or para positions. 1,4-Benzoquinone, for example, can be made from the oxidation of hydroquinone, p-aminophenol or p-phenylenediamine, or sometimes from quinic acid. The reagents generally used for the oxidation are dichromate/sulfuric acid mixture, ferric chloride, silver (II) oxide, ceric ammonium nitrate or sodium hypochlorite/phase transfer catalyst mixture. Such methods are generally performed in solvents which may need elaborate waste disposal procedures. Some processes may also take several hours for completion of the reaction. Thus, there is a continuing interest in identifying improved and cost-effective methods to prepare quinones, especially those with relatively complex structures.

Accordingly, it is an object of this invention to identify a simple process for the oxidation of aromatic dihydroxy compounds to the respective quinones.

It is yet another object of this invention to provide a method of producing quinones from appropriate starting materials using reagents that are fairly widely available.

It is a further object of this invention to find a process to prepare quinones without necessarily needing the addition of external solvents or reagents.

It is a still further object of this invention to provide a novel process of preparing quinones from the corresponding hydroquinones by a cost-effective process.

SUMMARY OF THE INVENTION

The present invention includes a method for producing quinones from hydroquinones by using sulfuryl chloride as the oxidizing agent. Considering the fact that sulfuryl chloride is a widely used reagent for halogenating or sulfonylating aromatic compounds including hydroxy aromatics, the present process surprisingly offers a heretofore unknown oxidation of hydroquinones to quinones without any substantial side reactions including halogenation. The reaction proceeds remarkably smoothly, with yields in many cases up to 100%, and in most cases generally does not need a separate solvent; sulfuryl chloride is generally used in excess. The inventive method generally comprises: (a) bringing together the hydroquinone and sulfuryl chloride in a molar ratio range of about 1:2 to 1:5 respectively in a suitable apparatus; (b) stirring or otherwise suitably mixing them at a temperature range between ambient and reflux temperature of sulfuryl chloride (which is about 69° C.) for about 0.1–10 hours; (c) removing any excess sulfuryl chloride, as well as the by-products $SO_2$ and HCl; and (d) isolating the product by filtration or other suitable means. The inventive process is particularly suitable for preparing hindered quinones.

DESCRIPTION OF THE PREFERRED EMBODIMENTS

In one embodiment, the present invention offers a method to oxidize hydroquinones to the corresponding quinones. The term "hydroquinone" herein refers to any 1,4-dihydroxy as well 1,2-dihydroxy substituted or equivalently substituted aromatic ring. Examples are the dihydroxybenzenes, the dihydroxynaphthalenes, dihydroxyanthracenes, dihydroxyphenanthracenes and the like. The oxidant that is useful to accomplish this transformation is sulfuryl chloride, $SO_2Cl_2$. $SO_2Cl_2$ is a well known reagent useful for halogenations and sulfonylation reactions, and has been used on a variety of compounds for those purposes. See, for example, H. Moore et al, *J. Amer. Chem. Soc.*, Vol. 93, 2812 (1971); M. Kharasch et al, ibid., Vol. 73, 964 (1951); idem., ibid., Vol. 61, 3432 (1939); J. March, *Advanced Organic Chemistry*, 3rd ed., pages 529, 532, 550, 621, 626 and 725, John Wiley & Sons, New York (1985); Tabushi et al, in *Synthetic Reagents*, Pizey, ed., Vol. 4, pp. 336–396 (John Wiley & Sons, New York (1981); *Bull. Chem. Soc. Japan.*, Vol. 37, 12380 (1964) and Vol. 38, 252 (1965); and D. Tarbell et al, *Org. Synthesis*, Coll. Vol. III, 267 (1955). Use of $SO_2Cl_2$ as an oxidant is not known heretofore. In view of that, applicants present invention, wherein $SO_2Cl_2$ was found to oxidize aromatic dihydroxy compounds into the corresponding quinones in a simple reaction process without resulting in halogenation or sulfonylation, was highly surprising.

The inventive method generally comprises: (a) bringing together the hydroquinone and sulfuryl chloride in a molar ratio range of about 1:2 to 1:5 respectively in a suitable apparatus; (b) stirring or otherwise suitably mixing them at a temperature range between ambient (about 20°–28° C.) and reflux temperature of sulfuryl chloride (which is about 69° C.) for a time period of about 0.1–10 hours; (c) removing any excess sulfuryl chloride and by-products $SO_2$ and HCl; and (d) isolating the product by filtration or other suitable means. Generally another solvent is not needed in the reaction. If one is preferred, any suitable solvent such as toluene, xylene, chlorobenzene and the like may be used. Typically, $SO_2Cl_2$ itself is used both as the reagent and as the solvent. The general molar ratio of the hydroquinone to $SO_2Cl_2$ is given above; the preferred ratio range is about 1:2 to about 1:4, while the typical ratio range is about 1:2 to about 1:3. Generally, the two ingredients are taken together in a suitable apparatus at about the ambient temperature. An inert atmosphere is generally not required. Generally, the ingredients are mixed well and kept at a temperature ranging from ambient temperature to about the reflux; the preferred range is ambient to about 60° C., and typical range is about 45° C. to about 60° C. Stirring is not necessary, although it may be preferred in some specific cases. The mixing and keeping are done for a time period of about 0.1–10 hours generally, 0.1–4 hours preferably and 0.1–1 hour typically. At the end of this time period, there is usually a color change to a bright yellow/orange color typical of a quinone compound. Isolation of the material may be performed by processes well known to those skilled in the art. In one approach, the by-products $SO_2$ and HCl may be removed by a suitable process, the apparatus may then be cooled, and the desired quinone may be isolated by pouring the contents, with stirring, into a nonsolvent such as, for example, water, ethanol, methanol, isopropanol, butanol and the like or mixtures thereof, in order to precipitate the quinone compound. The nonsolvent may contain other ingredients such as, for example, an alkali. Alternatively, one may remove any excess $SO_2Cl_2$, $SO_2$ and HCl, e.g., by vacuum distillation, and the residue may then be cooled and poured, with stirring if necessary, into a suitable nonsolvent to precipitate the quinone. The product may then be isolated, e.g., by filtration, and further purified by techniques known to those skilled in the art such as, for example, recrystallization, sublimation and the like. Yields of 70% to quantitative amounts based on the dihydroxy starting material are usually achieved. The pure quinone compound may be analyzed by conventional techniques such as, for example, elemental analysis, IR and NMR spectroscopy.

The process may be illustrated by the following description of the synthesis of 2,6-di-tert-butyl-1,4-benzoquinone. In a suitable flask fitted with a reflux condenser, 2,6-di-tert-butyl-1,4-hydroquinone and $SO_2Cl_2$ were taken in a 1:2 molar ratio respectively. The flask was then lowered into a heating medium such as, for example, an oil bath, steam bath, sand bath and the like, and heated, with occasional mixing, to reflux conditions. If desired, one may have a suitable stirrer during this stage, but it is not necessary. After approximately 30–120 minutes of so refluxing, the contents of the flask darkened in color, whereafter the flask was taken out of the heating bath, cooled, and the contents were poured into aqueous ethanol to precipitate 2,6-di-tert-butyl-1,4-benzoquinone. Yields of 80–100% based on the hydroquinone were obtained, with satisfactory analytical data.

The following Examples are provided in order to further illustrate the present invention; however, the invention is in no way limited thereby.

EXAMPLES

Example 1

Preparation of 2,6-di-tert-butyl-1,4-benzoquinone from 2,6-di-tert-butyl-1,4-hydroquinone:

In a single neck 500 ml round-bottomed flask equipped with a reflux condenser, 2,6-di-tert-butyl-1,4-hydroquinone (46.8 g, 0.21 mole) and $SO_2Cl_2$ (56.8 g, 33.8 ml, 2 equiv.) were mixed into a suspension. The flask with the suspension was lowered into an oil bath which was then heated sufficiently to let the contents reflux gently (bath temp. approximately 80° C.). After about 30 minutes of reflux, the contents had turned into a dark viscous mass, which after an additional one hour of reflux turned into a bright yellow-orange mass. The flask was then cooled to ambient temperature, the solid was broken up using a glass rod and the contents were poured into an Erlenmeyer flask (1 liter size) containing aqueous ethanol (50% v/v; 500 ml). The mixture was agitated vigorously and the precipitated yellow solid was filtered (Whatman #40 filter paper on a Buchner funnel). It was then dried in vacuo to yield the desired 2,6-di-tert-butyl-1,4-benzoquinone (46.5 g, >98% yield). The product was quite pure, but it was further recrystallized from aqueous ethanol (75%) to yield the pure quinone, m.p. 151°–152° C.; analytical data were consistent. It was noteworthy that no product or by-product that could be due to chlorination or sulfonylation by the $SO_2Cl_2$ was observed.

Examples 2–7

Using the procedure outlined in Example 1, the following benzoquinones (Table 1) were prepared from the corresponding hydroquinones. As in Example 1, no chlorinated or sulfonylated product or by-product was formed in these Examples too.

TABLE 1

| Example | Hydroquinone | Benzoquinone |
|---|---|---|
| 2 | 1,4-dihydroxybenzene | 1,4-Benzoquinone |
| 3 | 2-Chloro-1,4-dihydroxybenzene | 2-Chloro-1,4-benzoquinone |
| 4 | 2,5-Dichloro-1,4-dihydroxybenzene | 2,5-Dichloro-1,4-benzoquinone |
| 5 | 2,5-Dibromo-3-isopropyl-6-methyl-1,4-dihydroxybenzene | 2,5-Dibromo-3-isopropyl-6-methyl-1,4-benzoquinone |
| 6 | 2,3,5,6-tetrachloro-1,4-dihydroxy benzene | 2,3,5,6-tetrachloro-1,4-benzoquinone |
| 7 | 2,3,5,6-tetrabromo-1,4-dihydroxybenzene | 2,3,5,6-tetrabromo-1,4-benzoquinone |

What is claimed is:

1. A process to prepare aromatic quinones from corresponding dihydroxy aromatic compounds, said process comprising: (a) preparing a mixture of said dihydroxy aromatic compound and sulfuryl chloride in a molar ratio range of about 1:2 to 1:5 respectively in a suitable apparatus in a substantial absence of added solvent; (b) subjecting said mixture to a temperature range between ambient temperature and reflux temperature of sulfuryl chloride for a time period of about 0.1–10 hours; and (c) isolating said quinone.

2. The process according to claim 1, wherein said molar ratio range in step (a) is about 1:2 to about 1:3.

3. The process according to claim 1, wherein said temperature is about the reflux temperature of sulfuryl chloride.

4. The process according to claim 1, wherein said time period is about 0.1–5 hours.

5. The process according to claim 1, wherein said time period is about 0.1–2 hours.

6. The process according to claim 1, wherein said isolation comprises: (a) removing sulfuryl chloride to leave behind a residue; (b) adding said residue to a suitable nonsolvent to precipitate said quinone; and (c) filtering said quinone.

7. The process according to claim 6, wherein said nonsolvent is selected from the group consisting of water, ethanol, methanol, isopropanol, butanol, aqueous alkali, alcoholic alkali, and mixtures thereof.

8. The process according to claim 1, wherein said isolation comprises addition to a suitable nonsolvent to precipitate said quinone and filtering said quinone.

9. The process according to claim 8, wherein said nonsolvent is selected from the group consisting of water, ethanol, methanol, isopropanol, butanol, aqueous alkali, alcoholic alkali, and mixtures thereof.

10. The process according to claim 1, wherein said aromatic quinone is selected from the group consisting of 1,4-benzoquinone, 1,2-benzoquinone, 1,4-naphthoquinone, 4,4-diphenoquinone, 2,6-naphthoquinone, 5,9- anthraquinone, 2,6-di-tert-butyl-1,4-benzoquinone, 2,3,5,6-tetrabromo-1,4-benzoquinone, 2,3,5,6-tetrachlorobenzoquinone, and 2,5-dibromo-3-propyl-6-methyl-1,4-benzoquinone.

11. The process according to claim 10, wherein said aromatic quinone is 1,4-benzoquinone.

12. The process according to claim 10, wherein said aromatic quinone is 2,6-di-tert-butyl-1,4-benzoquinone.

13. A process to prepare 1,4-benzoquinone from corresponding 1,4-dihydroxybenzene, said process comprising: (a) preparing a mixture of said dihydroxybenzene and sulfuryl chloride in a molar ratio range of about 1:2 to 1:5 respectively in a suitable apparatus; (b) subjecting said mixture to a temperature range between ambient temperature and reflux temperature of sulfuryl chloride for a time period of about 0.1–10 hours; and (c) isolating the 1,4-benzoquinone.

14. A process to prepare 2,6-di-tert-butyl-1,4-benzoquinone from 2,6-di-tert-butyl-1,4-dihydroxybenzene, said process comprising: (a) preparing a mixture of said dihydroxybenzene and sulfuryl chloride in a molar ratio range of about 1:2 to 1:5 respectively in a suitable apparatus; (b) subjecting said mixture to a temperature range between ambient temperature and reflux temperature of sulfuryl chloride for a time period of about 0.1–10 hours; and (c) isolating 2,6-di-tert-butyl-1,4-benzoquinone.

15. The process according to claim 14, wherein said molar ratio range is 1:2, said temperature in step (b) is the reflux temperature of sulfuryl chloride, and said time period is 0.1–2 hours.

* * * * *